United States Patent [19]

Kanebako et al.

[11] Patent Number: 5,135,306

[45] Date of Patent: Aug. 4, 1992

[54] PARTICLE MEASURING METHOD AND APPARATUS

[75] Inventors: Makoto Kanebako, Tsukuba; Muneharu Ishikawa, Ryuugasaki, both of Japan

[73] Assignee: Kowa Company Ltd., Japan

[21] Appl. No.: 413,538

[22] Filed: Sep. 27, 1989

[30] Foreign Application Priority Data

Sep. 30, 1988 [JP] Japan .................................. 63-244250
Oct. 25, 1988 [JP] Japan .................................. 63-267274

[51] Int. Cl.$^5$ ............................................ G01N 21/00
[52] U.S. Cl. ...................................... 356/336; 356/339; 356/369; 250/574
[58] Field of Search ............................ 356/335-343, 356/370, 364, 369, 237; 350/564, 574

[56] References Cited

U.S. PATENT DOCUMENTS

| | | | |
|---|---|---|---|
| 4,457,624 | 7/1984 | Goldberg et al. ............... | 356/336 |
| 4,696,571 | 9/1987 | Goldberg et al. ............... | 356/336 |
| 4,830,494 | 5/1989 | Ishikawa et al. ............... | 250/574 |
| 4,893,932 | 1/1990 | Knollenberg ................... | 356/257 |

Primary Examiner—Richard A. Rosenberger
Assistant Examiner—Hoa Pham
Attorney, Agent, or Firm—Bruce L. Adams; Van C. Wilks

[57] ABSTRACT

Disclosed is a particle measurement method and apparatus for measuring particle properties in which a laser beam is projected into a detection region in a medium containing particles to be measured, and a photoelectric detector having a predetermined dynamic range is used to detect the laser light scattered by the particles in the medium to produce signals which are evaluated to measure the particle properties. The polarization of the laser beam and the intensity of the scattered light are regulated in accordance with the range of particle sizes measured so that the intensity of the scattered light is within the dynamic range of the photoelectric detector. This arrangement makes it possible to expand the range of particle sizes with an improved resolving power in particle measurement without multi-valued ranges.

9 Claims, 11 Drawing Sheets

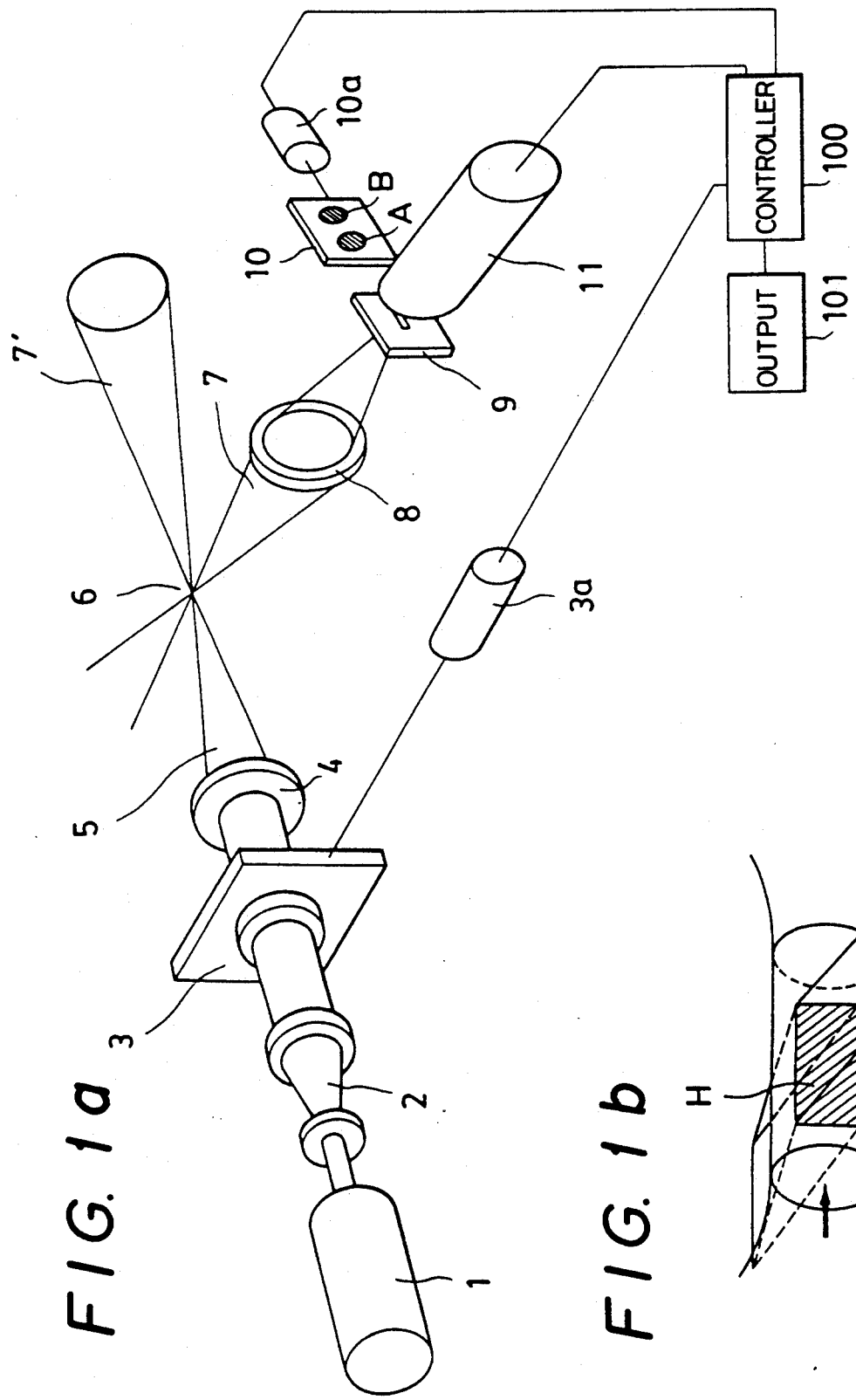

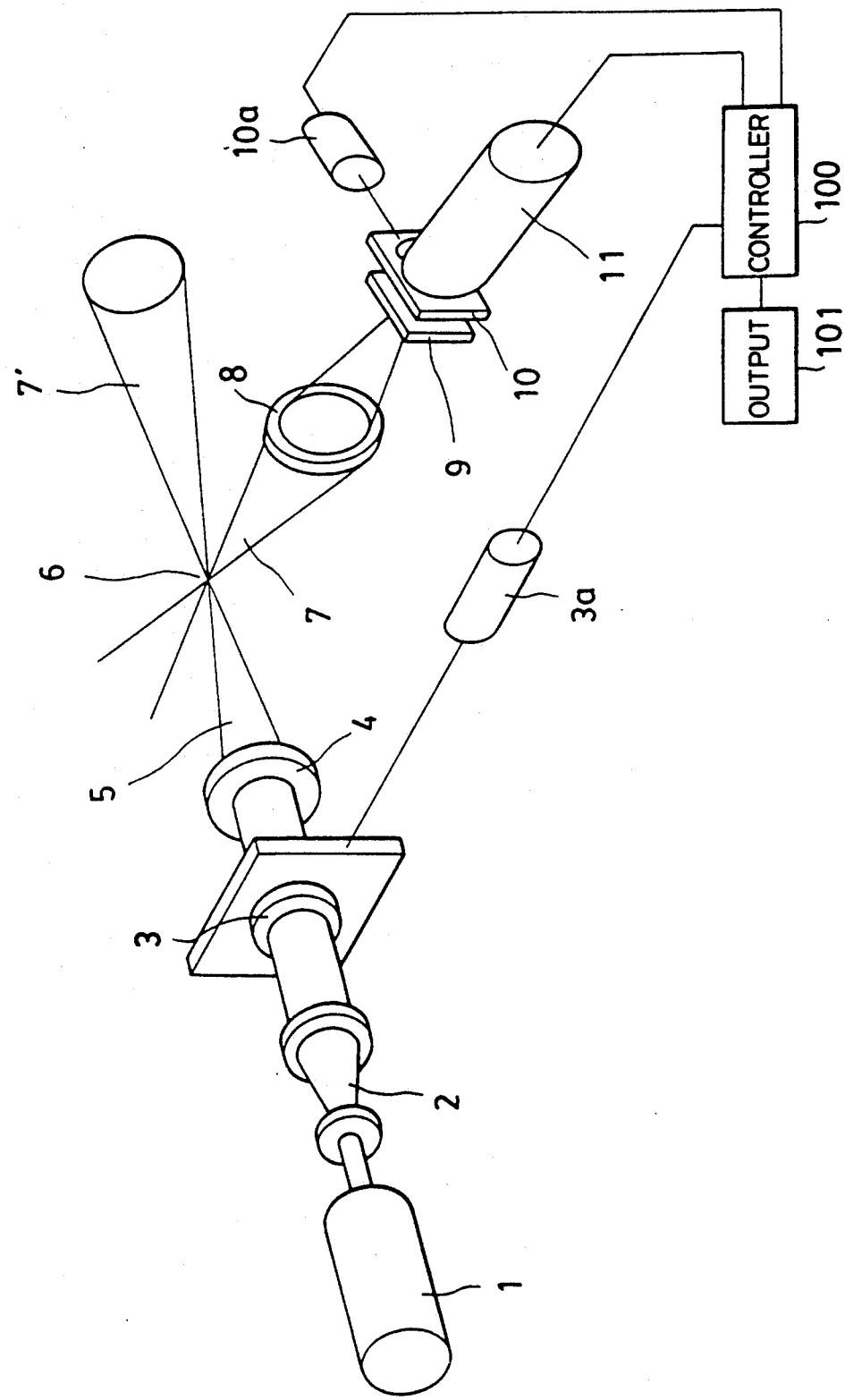

PARTICLE MEASURING METHOD AND APPARATUS

BACKGROUND OF THE INVENTION

1. Field of the Invention

This invention relates to a particle measuring method and apparatus, and more particularly to a particle measuring method and apparatus in which a laser beam is used to illuminate a detection zone in a medium, laser light scattered by particles in the medium is detected by a photosensor and measurement is effected by measuring particle properties based on output signals from the photosensor.

2. Description of the Prior Art

Apparatuses are known for optically measuring particles in a liquid or gaseous medium by utilizing scattered light. With such apparatuses, particles are measured by using light receiving elements to evaluate the scattering of the laser light that impinges on the liquid or gas concerned (See for example Japanese Laid open Publication No. 64-18043). However, because the light scattered by the particles has a very low intensity, it is necessary to use means to ensure that scattered light impinging on the light receiving element is of a sufficiently high intensity.

This usually consists of controlling the intensity or polarization of the incident light, or the direction in which the scattered light is received. Conventional methods include utilizing all of the laser light that has been randomly polarized as the incident light or, in the case of linearly polarized laser light, arranging the polarization to be perpendicular to the scattering plane for the measurement.

When the linearly polarized incident light oscillates perpendicularly with respect to a plane obtaining between the axial orientation of the incident light and the axial orientation along which the scattered light is received ( the scattering plane ), it is referred to as S-polarized light, and when the oscillation of the incident light is parallel to the scattering plane, it is referred to as P-polarized light.

Particularly in the case of apparatuses for determining particle size by measuring the intensity of laterally scattered light from particles in a liquid that are irradiated with a beam of laser light, linearly polarized laser light is picked up as S-polarized light, when particles are 0.1 microns or smaller, because the contribution of the P-polarized incident component from laterally scattered light is negligibly small compared to the S-polarized incident component.

FIG. 2a illustrates the relationship between scattered light intensity and particle size in accordance with one example in which monochromatic light is used. Up to a particle size of around 0.3 microns the scattered light intensity is a single-valued function of particle size, but above that size this function does not obtain. More specifically, below 0.3 microns precise measurement is possible because there is a 1:1 correspondence between the scattered light intensity and particle size, but above that size this becomes impossible. This means that 0.3 microns is the effective limit of measurable particle size.

In this regard, conventional methods that have been used include eliminating multiple values by using a light source for producing polychromatic light, or expanding the single-valued zone to the size of the larger particles by measuring the intensity of forwardly scattered light. However, in order to cover a wide range of particle sizes including 0.1 microns and below, the use of lateral scattering is indispensable to prevent stray light in the measurement cell, and also in order to utilize the convergency of the laser light it has become necessary to expand the range of measurable particle sizes on the basis of the lateral scattering method that utilizes the monochromaticity of the laser beam.

When the incident laser light is set to be P-polarized light, a single-valued function obtains even when the particle size is above 0.3 microns, but then the dynamic range of the photosensor becomes a problem.

The photosensor usually has a usable dynamic range which limits the range of scattered light intensities. As such, even if the range of particle sizes in which a single-valued function obtains is expanded, it becomes impossible to process the signals.

On the other hand, one arrangement is used to reduce the background light due to a medium in the scattered light measurement zone by providing an optical mask in the light detecting system. An automatic alignment is also possible whereby in accordance with the output of the photosensor the mask is located at the optimum position in relation to the focal depth of the imaging lens or scattered light measurement zone. Such a mask alignment system is disclosed in Japanese Laid-open Patent Application No. 64-18043 above mentioned. In such an apparatus, when the amount of scattered light is reduced so that it matches the dynamic range of the photosensor, there occurs the risk that it will prevent accurate operation of the automatic mask alignment system described above.

Further, it is known that a photon counting method is preferably used to detect a very weak intensity of light scattered from a single particle smaller than 0.1 microns in diameter ( see for example U.S. Pat. No. 4,830,494). Since this photon counting method employ a digital processing, stable signals are obtained against outer electrical disturbance, thus enabling precise particle measurement. The photon counting method is, however, impractical for measuring particles whose diameter ranges above 0.1 microns, for example, because a too strong intensity of scattered light is received by the photosensor.

SUMMARY OF THE INVENTION

It is, therefore, an object of the present invention to provide a particle measuring method and apparatus being capable of measuring particle sizes accurately by classifying the particles into a finely graded size distribution.

It is another object of the present invention to provide a particle measurement apparatus that can be adapted to measure a wide range of particle sizes without any adverse effect on optical mask alignment.

It is still another object of the present invention to provide a particle measuring method and apparatus being capable of measuring particle sizes accurately using a photon counting method.

According to the invention, a particle measurement method for measuring particle properties is disclosed. A laser beam is projected into a detection region in a medium containing particles to be measured. A photoelectric detector having a predetermined dynamic range is used to detect the laser light scattered by the particles in the medium and produces signals which are evaluated to measure the particle properties. The inventive method includes the steps of measuring particle sizes, classifying the particle sizes measured into first and second ranges, regulating the polarization of the laser beam depending upon whether the particle size measured belongs to the first or second range, and regulating the intensity of the scattered light so as to be within the dynamic range of the photoelectric detector when the particle size belongs to the second range.

In a particle measuring apparatus according to the invention, there are provided means for regulating the polarization of the laser beam, means for regulating the intensity of the scattered light impinging on the photoelectric detector, means for measuring particle sizes in accordance with the signals from the photoelectric detector, and means for controlling the laser beam polarization and the intensity of the scattered light in accordance with the range of particle sizes measured so that the intensity of the scattered light is within the dynamic range of the photoelectric detector.

Such an arrangement enables the control of the polarization of laser light and the intensity of the scattered light detected by the photoelectric detector. This enables the scattered light intensity and laser light polarization conditions to be suitably set in accordance with the range of particle sizes to be measured. That is, measurement conditions can be set appropriately, taking into consideration factors involved such as, for example, the dynamic range of the photoelectric sensing element and the intensity of the light scattered by the particle that has multi-valuedness in terms of the particle size.

With such an arrangement, it is thus possible to control the laser light polarization and the intensity of the light that impinges on the photosensor. Since this enables the intensity distribution of the particle scattered light to have the single-valuedness in terms of the particle size and the intensity of scattered light to be within the dynamic range of the photoelectric detector, the capabilities of the measurement system can be used to the full. This enables a wide range of particle sizes to be measured with a very high resolution.

Preferably, the polarization of the laser beam is regulated to be S-polarized when the particle size measured is below a predetermined value and P-polarized when it exceeds the predetermined value. In a preferable embodiment, filter means having a plurality of filters each having a different transmittance are provided, and a predetermined filter is selected to regulate the intensity of the scattered light in accordance with a predetermined range of the particle sizes so that the intensity of the scattered light is within the dynamic range of the photoelectric detector.

In such an arrangement, the filters serve to attenuate the intensity of scattered light, thus enabling the use of the photon counting method for a whole range of particle size resulting in an improvement in measurement accuracy.

A particle measurement apparatus according to the invention comprises a mask disposed in front of the photoelectric detector to limit the scattered light that impinges thereon, mask alignment means for aligning the mask to an optimum position, filter means having a plurality of filters each having a predetermined transmittance to regulate the intensity of the scattered light that impinges on the photoelectric detector, and means for selecting one of the filters without attenuation of light during mask alignment and one of the filters with a predetermined transmittance after mask alignment so that the intensity of the scattered light comes within the dynamic range of the photoelectric detector.

With such an arrangement, scattered light intensity is regulated so that it matches the dynamic range of the photoelectric detector used for measuring the scattered light intensity during the measurement process. In this arrangement, precise mask alignment is maintained even when the regulation of the scattered light intensity results in a considerable reduction in the amount of light because the mask alignment can be effected using a filter without attenuation.

BRIEF DESCRIPTION OF THE DRAWINGS

The objects and features of the present invention will become more apparent from the accompanying drawings and the following detailed description of the invention.

FIG. 1a is an explanatory drawing showing the basic structure of the particle measurement apparatus according to the present invention;

FIG. 1b is an enlarged view of the measurement zone of the apparatus with particles passing through a hatched zone H;

FIG. 3 shows another embodiment of the apparatus of FIG. 1a;

DETAILED DESCRIPTION OF THE PREFERRED EMBODIMENTS

Figure 2A:
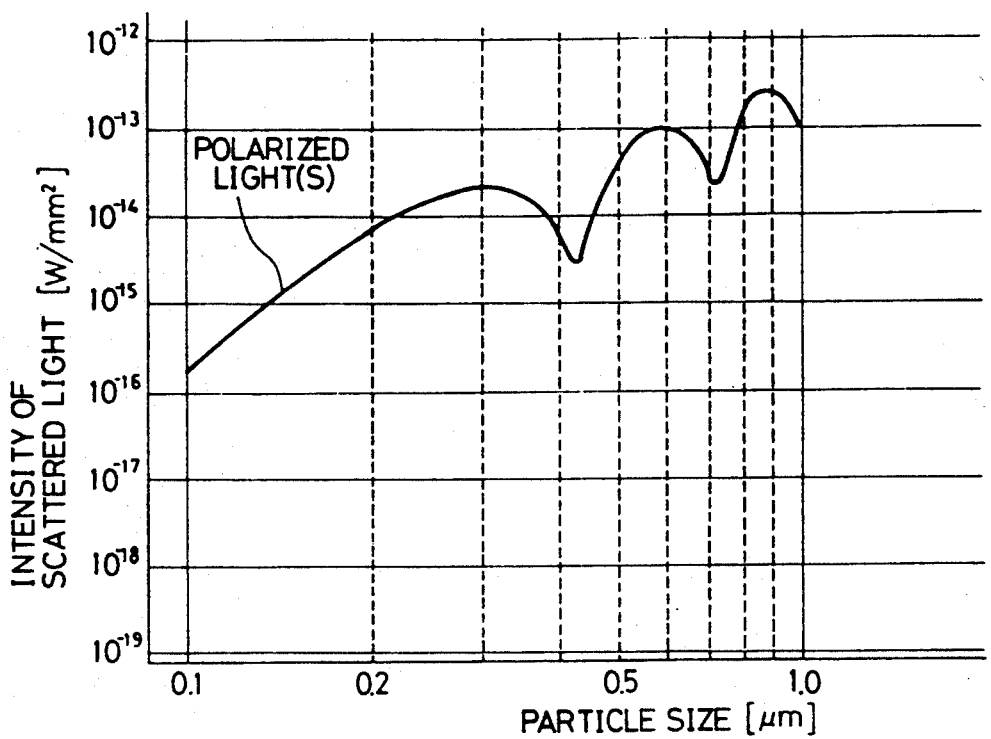
FIGS. 2a and 2b are graphs showing the relationship between particle size and the scattered light intensity for different polarization conditions.

Details of the invention will now be described with reference to the illustrated embodiments.

First, the basic structure of the particle measurement apparatus according to the present invention will be described with reference to FIG. 1.

FIG. 1a shows the structure of the optical and control systems of the apparatus. In the drawing reference numeral 1 denotes a laser light source such as a semiconductor laser for emitting a laser beam having a linear polarization, A beam expander 2, a half-wave plate 3 for varying the direction of linear polarization, and a converging lens 4 are provided along the axis of the light emitted by the laser light source 1, and the laser beam 5 thus emitted is focused to a point 6. The laser beam 5 can be formed into S-polarized light by removing the half-wave plate 3 from the optical path of a light-converging system, described below, or into P-polarized light by inserting the half-wave plate into the optical path.

The measurement zone H in FIG. 1b is located within the beam waist at the focusing point 6 in the sample liquid or gas medium (not illustrated) containing the particles to be measured. The light-receiving system which includes of elements 8 to 11 for detecting laterally scattering light is disposed substantially at 90 degrees to the direction of the incident laser beam. Specifically, the light-receiving system comprises an imaging lens 8 for forming scattered light into an image at a mask 9, and a photosensor 11 such as a photomultiplier serving as a photoelectric detector. The mask 9 is to ensure that only the required scattered light component around the focusing point 6 impinges on the photosensor 11.

FIG. 1b shows an enlargement of the measurement zone of the light beam at the point 6. The hatched portion H shows the extent and shape of the mask 9 aperture obtained by image projection by means of the imaging lens 8. This zone is set so that light scattered by particles passing through the zone is received by the photosensor 11 as particle optical information.

In this embodiment, a neutral density (ND) filter 10 serving as a light attenuator means can be inserted into or removed from the light path between the mask 9 and the photosensor 11. The ND filter 10 is inserted and retracted by the operation of mechanical actuators such as a motor, solenoids and so forth. The ND filter 10 is comprised of ND filters A and B which have different transmittances. When the ND filter 10 is to be inserted into the optical path, filter A or filter B is selected as required by an actuator 10a, as described below.

The actuator 10a is controlled, in accordance with the following measurement process, by a controller 100 which consists of a microprocessor, memory and other elements. The controller 100 calculates the particle diameter, as described below, from the data output by the photosensor 11 and outputs the result, in a prescribed format, to an output section 101, which can be a printer or display unit, for example. In the measurement process the ND filter 10 is inserted into or retracted from the optical path of the light-receiving system, as required. Also, the controller 100 can control the insertion/retraction of the half-wave plate 3 between the beam expander 2 and the converging lens 4 by means of the actuator 3a to set the polarization of the incident light beam to S-polarized light or P-polarized light.

Next, the principle of the particle measurement in the case of the present embodiment will be described. This embodiment differs from the conventional system in that it does not employ the same polarization conditions for the whole range of effective particle size measurement.

Figure 2B:
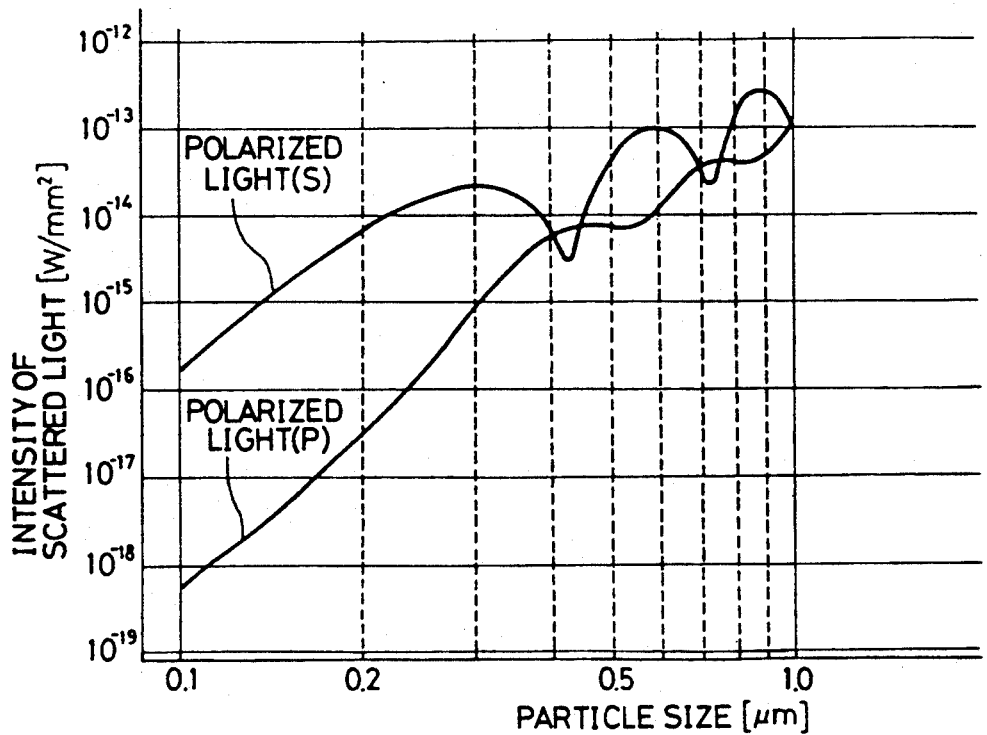

FIG. 2b shows an example of the relationship between particle size and the intensity of scattered S-and P-polarized light. The graph shows that in the case of S-polarized light, the single-valued property disappears when the size exceeds 0.3 microns, but when P-polarized light is used, the characteristic function is extremely close to being single-valued even in the case of particles of 1 micron or more. However, when particles are 0.2 microns or smaller, the intensity of P-polarized scattered light becomes extremely weak compared to when S-polarized light is used, i.e. less than hundredth as strong, which makes it difficult to separate it from background light.

Because of this, S-polarized light is used for measuring particles ranging in size from 0.1 to 0.2 microns, while for larger particles P-polarized light is used, the changeover to P-polarized light being effected by the insertion of the half-wave plate. When P-polarized light is being used and the particles are large, the ND filter 10 is interposed between the mask 9 and the photosensor 11 to reduce the intensity of the scattered light to bring it within the dynamic range of the photosensor 11.

Details will now be described of the setting of each of the parts required for above measurement using the apparatus of FIG. 1, starting with the half-wave plate.

Figure 4:
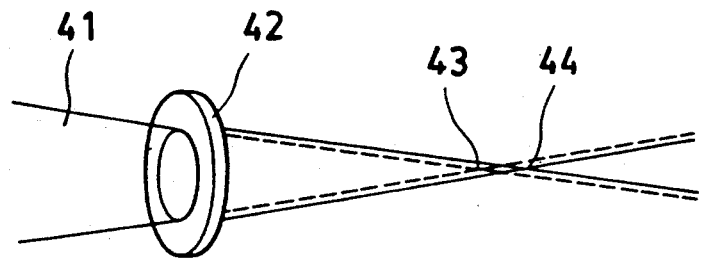
FIG. 4 shows the location of the half-wave plate.

The half-wave plate 3 is a plane parallel plate so that, as shown in FIG. 4, the beam angle is not changed by the passage of the light waves but the point of convergence changes if the half-wave plate is provided in the converging portion. That is, in FIG. 4 the point of convergence 43 of the laser light beam 41 shifts to the position denoted by reference numeral 44 when a half-wave plate 42 is inserted. However, the angle of the light beam remains constant whether the half-wave plate 42 is inserted or not, as illustrated by the solid and broken line.

Consequently, preferably the half-wave plate will be provided at a position where the light waves are parallel. With reference to FIG. 1, the optimum position is, as shown, between the beam expander 2 and the condenser lens 4, with respect to keeping changes in the point of convergence 6 to a minimum.

Figure 5A:
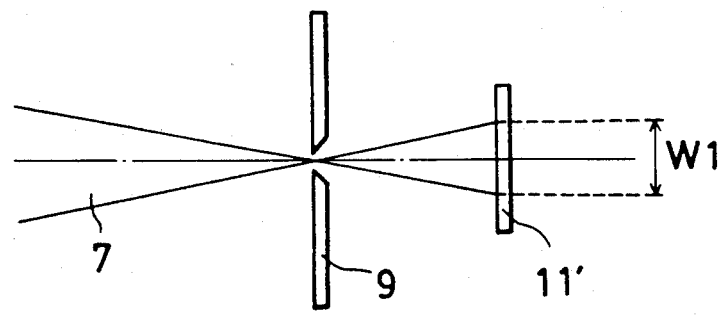
FIGS. 5a and 5b show the location of the ND filter.
Figure 5B:
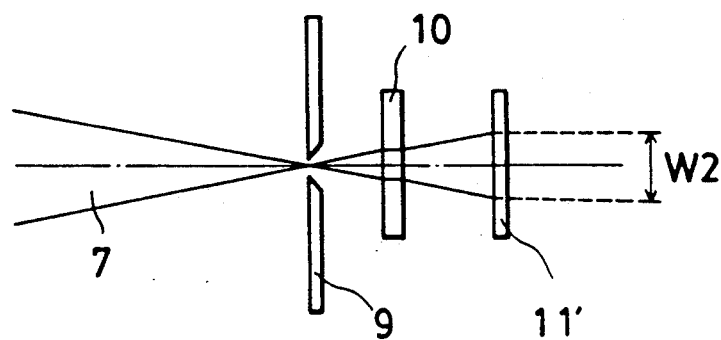

The ND filter also is a plane parallel plate and as such is preferably provided at a position where the laser light beam is parallel. The light beam is at its most parallel between the beam expander and the converging lens, but because it is not precisely parallel, there is a risk that the fitting of the filter plate in position may distort the point of convergence. Thus, in the case of the present apparatus the ND filter is provided, as shown in FIG. 3, between the mask 9 and the photosensor 11. By providing the ND filter 10 in this position, as shown in FIG. 5b, the beam width W2 on the measuring plane 11' of the photosensor 11 is narrower than prior to the provision of the ND filter 10 (FIG. 5a), so there is no adverse effect on the measurement.

If the scattered light intensity input is too large, the photoelectric detector will be saturated. The scattered light intensity may be thus high when the particles are large or when there are high particle concentrations. Here, in view of the fact that the apparatus involved will be used for measuring low particle concentrations, only the case of large particles will be considered.

Figure 6A:
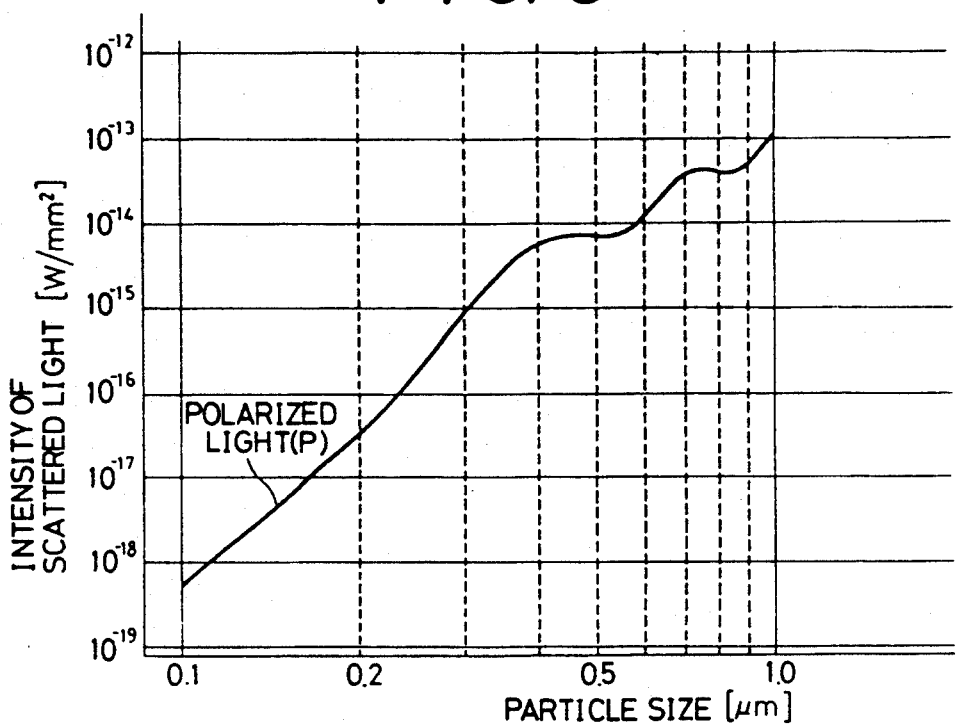
FIGS. 6a and 6b are graphs showing the relationship between particle size and scattered light intensity when using P-polarized light, and the same relationship following the insertion of the ND filter.
Figure 6B:
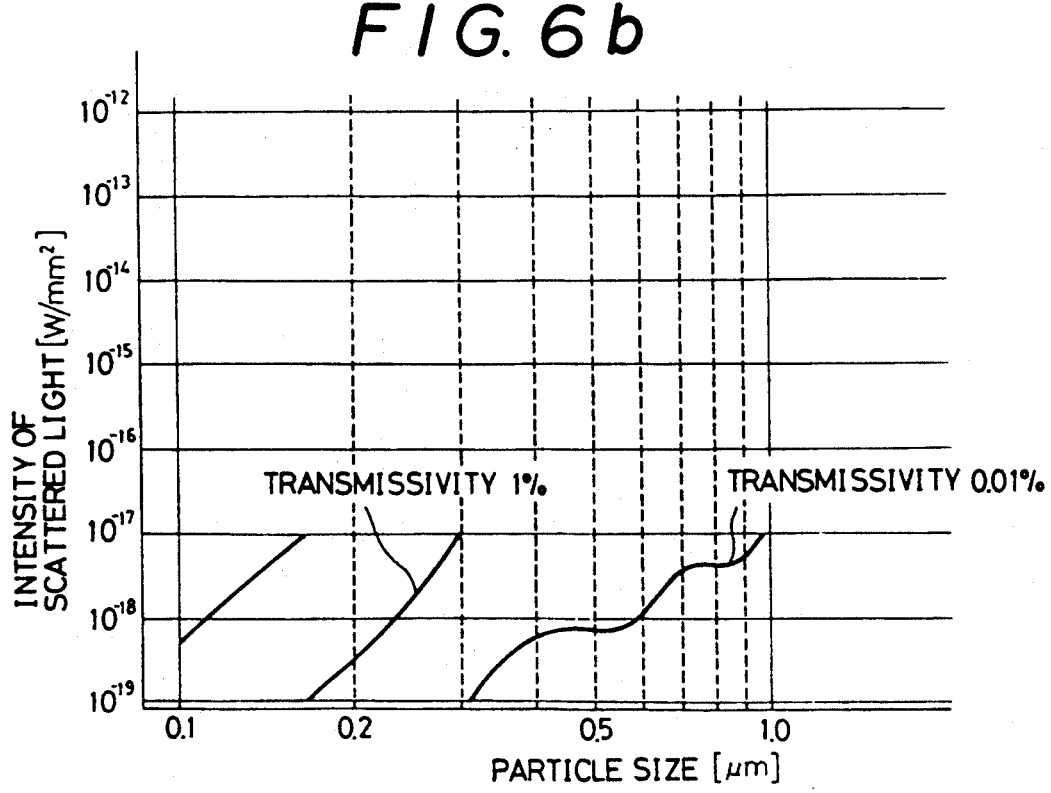

From FIGS. 6a and 6b it can be seen that as particles increase in size there is also an increase in the intensity of the scattered light. As a simple model, if the dynamic range (the range of light intensity that can be measured without saturation) of a measuring system constituted of the photosensor 11 and the controller 100 is 100, it can be seen from FIG. 6a that within the range 0.1 to 1.0 microns scattered light intensity W/mm$^2$) varies from $10^{-19}$ to $10^{-13}$.

Referring to FIG. 6b, the dynamics range is again 100. The above delineated particle size range divides into three scattered light intensity groups: $10^{-19}$ to $10^{-17}$, $10^{-17}$ to $10^{-15}$ and $10^{-15}$ to $10^{-13}$. Intensity in the range $10^{-19}$ to $10^{-17}$ can be measured by using linearly S-polarized laser light. For other ranges, the P polarized light is selected. An ND filter with transmittance of 1% is used for the $10^{-17}$ to $10^{-15}$ range and ND filter with a transmittance of 0.01% is used for the $10^{-15}$ to $10^{-13}$ range. Thus, it becomes possible to measure the particle sizes ranging from 0.1 to 1 micron within the dynamic range.

Figure 7:
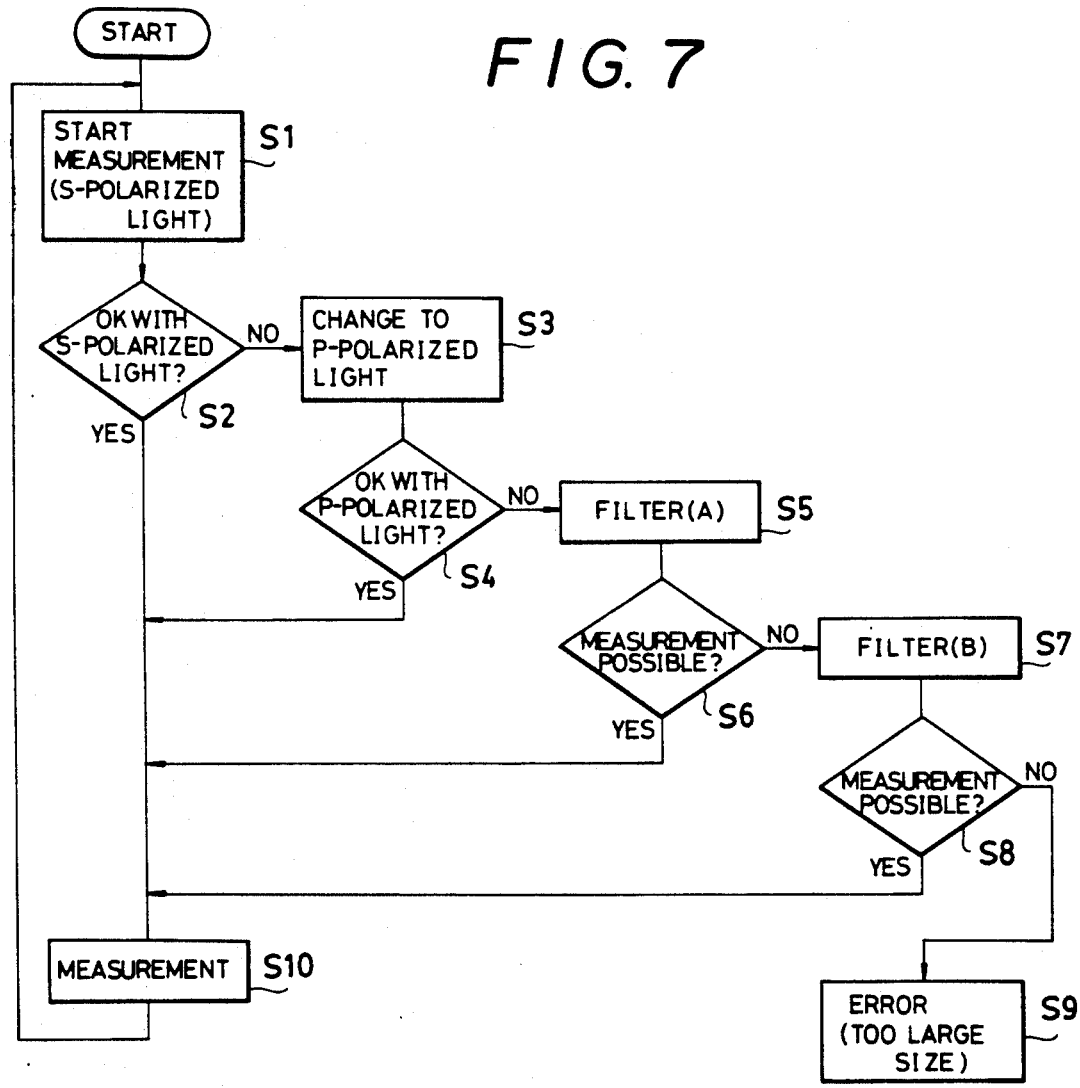
FIG. 7 is a flowchart of the measurement procedure according to the invention.

FIG. 7 is a flowchart of the measurement control process of the controller 100 in the apparatus shown in FIG. 1.

In step S1 the size of the particle is measured by counting the number of photoelectric pulses corresponding to the intensity of the scattered light acquired by the photoelectric detector 11 using a photon counting method; in the measurement initialization process the half-wave plate 3 is not inserted so as to use S-polarized light for measuring the scattered light intensity. Here the ND filter 10 is not yet interposed in the optical path.

In step S2 the measurement results of step S1 are evaluated. If the particles are small (little scattered light) and it is judged that measurement with S-polarized light is possible, in step S10 measurement proceeds using S-polarized light. If in step S2 it is judged that measurement is not possible with S-polarized light, the process moves to step S3, the half-wave plate 3 is interposed in the optical path to change to P-polarized light and the same measurement as in step S1 is performed.

In step S4 the measurement results of step S3 are evaluated to determine whether or not measurement with P-polarized light is possible. If it is judged that measurement is possible with P-polarized light, the process moves to step S10 and measurement is performed. If measurement with P-polarized light is not possible, then in step S5 the ND filter with the higher transmittance, which in the illustrated example is the ND filter A having a transmittance of 1% (FIG. 6), is used, and in step S6 the measurement is proceeded with, and it is judged in accordance with the degree of attenuation whether or not measurement is possible.

If in step S6 measurement is judged to be possible, the process moves to step S10. When measurement is judged to be impossible, in step S7 the ND filter having the lower transmittance, which in the illustrated example is the ND filter B having a transmittance of 0.01% (FIG. 6), is used, and in step S8 the measurement results are again evaluated. If in step S8 it is judged that measurement is possible with ND filter B, the process moves to step S10. If in step S8 it is judged that measurement is impossible, in step S9 it is determined that there is a measurement error and it is output to the measurement section 101 that measurement is impossible.

As in accordance with the above-described embodiment the intensity of the light scattered by the particles to be measured can be regulated to keep it within the dynamic range of the photosensor 11 by changing the polarization to alter the particle light-scattering conditions and by using ND filters to attenuate the intensity of the scattered light, the range of particle sizes that can be measured is considerably expanded. In addition, the particle resolving power of the system can be increased by suitably setting the polarization conditions so as to avoid multi-valued ranges.

Figure 8:
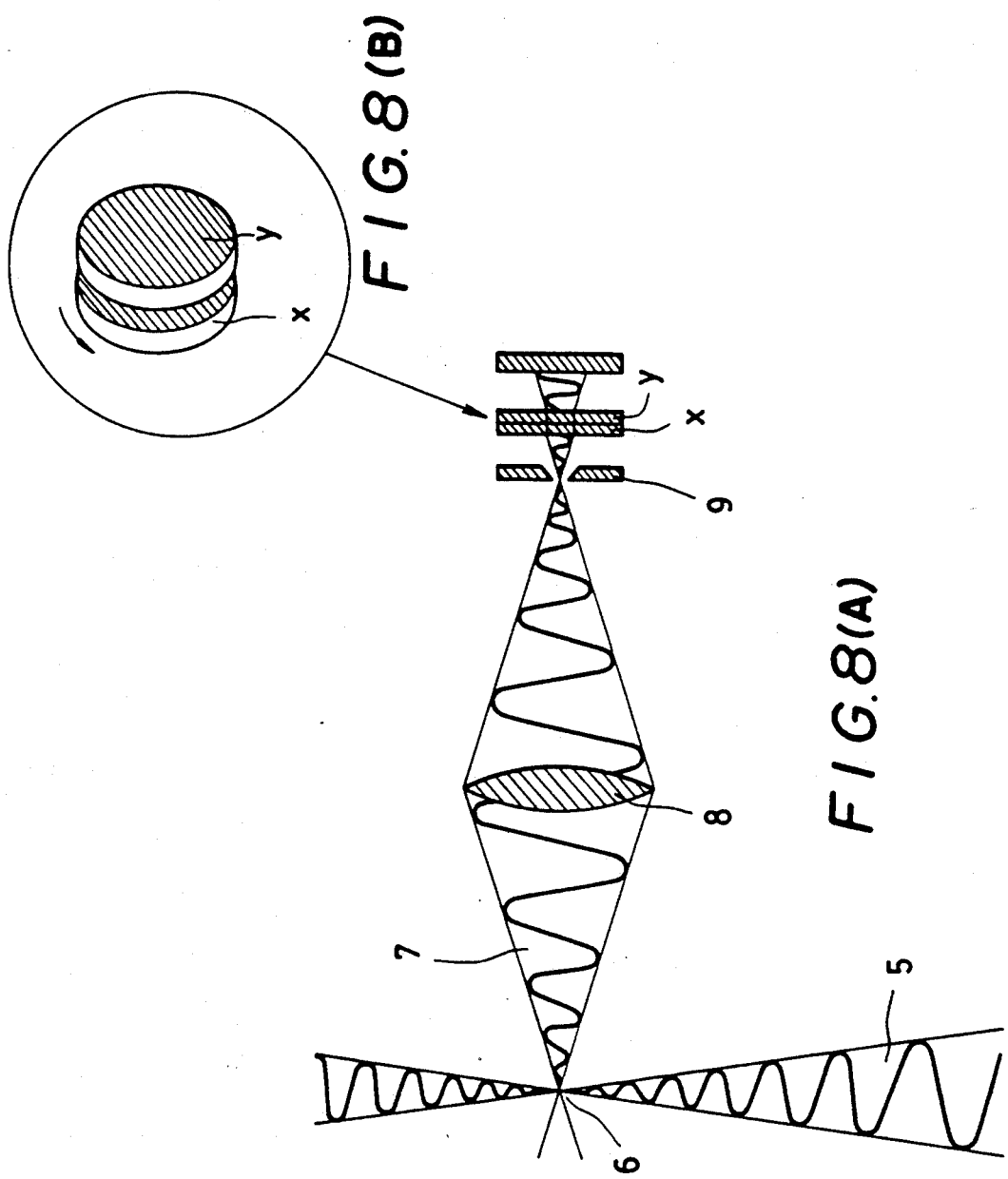
FIGS. 8A and 8B shows a variation of the scattered light intensity control system.

In the foregoing an ND filter is shown as the means used to provide the attenuation of the scattered light but, as shown in FIG. 8, instead of ND filter 10 a pair of polarizers X and Y may be employed.

The polarizer Y is fixed at an angle whereby the scattered light having passed therethrough is thereby set to the P-polarization light angle, while the polarizer X can be turned by an appropriate actuator so as to enable the attenuation to be varied continuously. As in this case the polarization characteristics of the scattered light change according to the different particle sizes, the angle of polarizer Y is fixed to limit the polarization of the passing light to a predetermined direction in order to facilitate the correspondence with the theoretical value.

Figure 9:
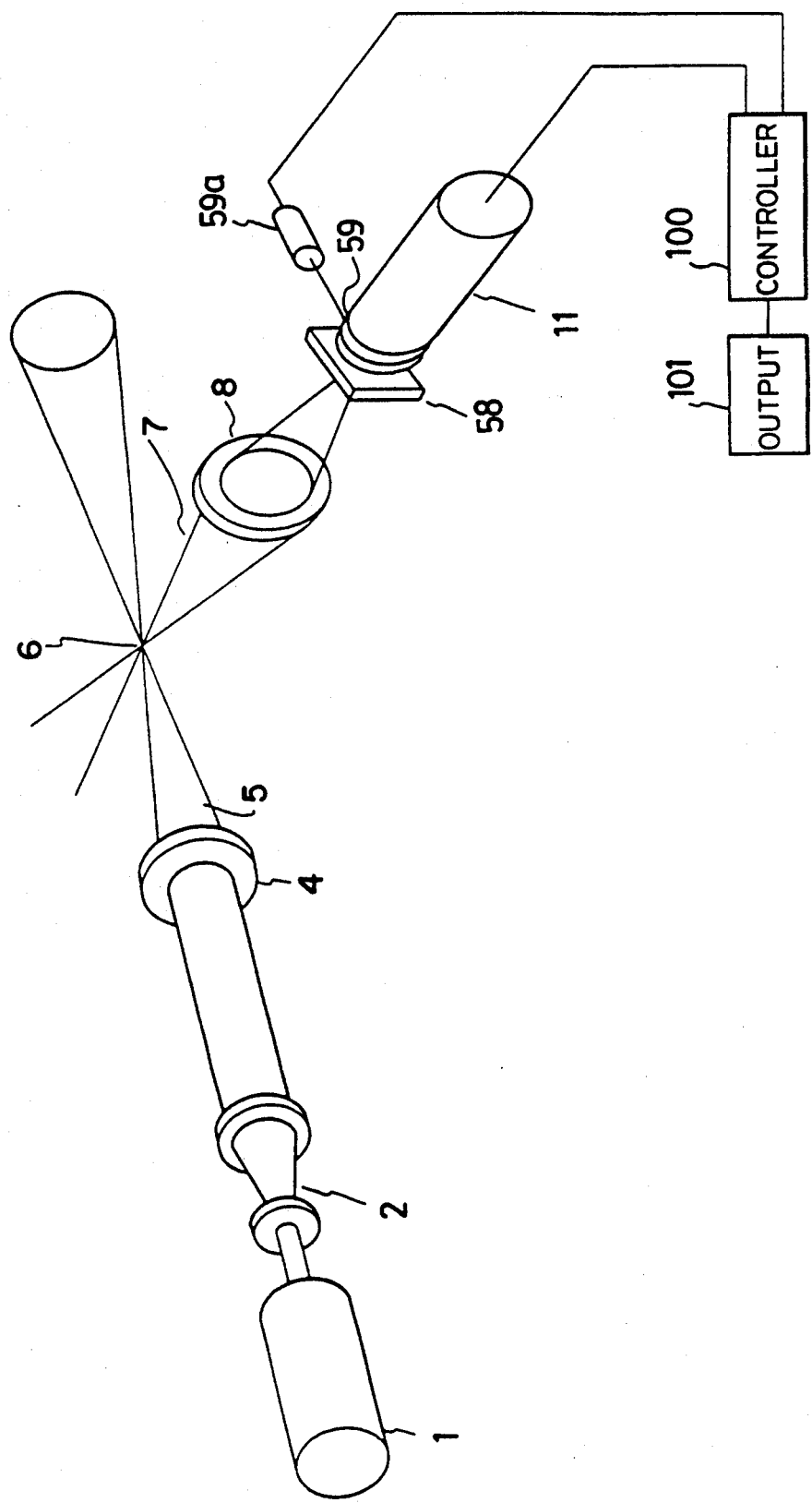
FIG. 9 is an explanatory drawing showing the basic structure of the particle measurement apparatus according to the present invention.

FIG. 9 shows another embodiment of the invention in which a wide range of particle sizes can be measured without any adverse effect on optical mask alignment. In the embodiment in FIG. 9, the same or similar portions as those in the embodiment of FIG. 1 are provided with the same reference numerals with their detailed description omitted.

In FIG. 9, an optical mask 58 is disposed in front of the photosensor 11 to limit the scattered light in the measurement zone. Thus, the mask 58 is to ensure that only the required scattered light component around the point 6 impinges on the photosensor 11. Further, a neutral density (ND) filter holder 59 serving as a light attenuator means can be inserted into or removed from the optical path between the mask 58 and the photosensor 11.

Figure 10:
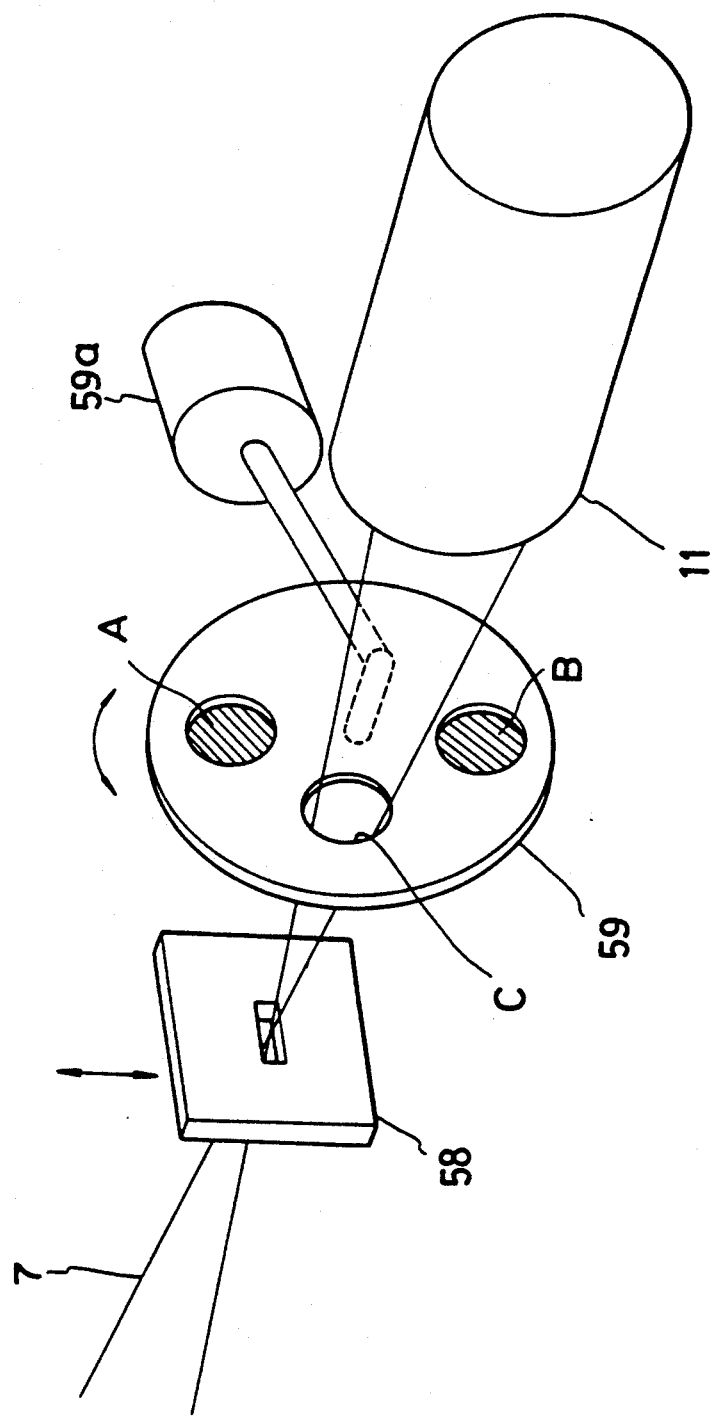
FIG. 10 shows the control system used for controlling the ND filter shown in FIG. 9.

As shown in FIG. 10, the ND filter holder 59 is a disk-shaped revolving type with multiple round apertures. In the embodiment that is illustrated, two of these apertures, A and B, are fitted with ND filters having different transmittances. The ND filter holder 59 is rotated by an actuator 59a to position either one of the filters A and B or an empty aperture C in the optical path. Thus, when aperture C is inserted in the optical path, there is no attenuation of the light. The intensity of the scattered light 7 entering the photosensor 11 is regulated by selecting one of the filters A and B, or the empty aperture C.

The actuator 59a is controlled, in accordance with the following measurement process, by the controller 100 which consists of a microprocessor, memory and other elements. The position of the mask 58 is adjusted vertically, as indicated by the arrow in the drawing, by means of a known mask alignment arrangement, under the control of the controller 100. This alignment is performed in accordance with known methods, for example, in accordance with the intensity of the output of the photosensor 11. The ND filter and the mask are positionally regulated in the measurement process. However, the regulation in transmittance of the ND filter disturbs the successful regulation of the mask.

Figure 11A:
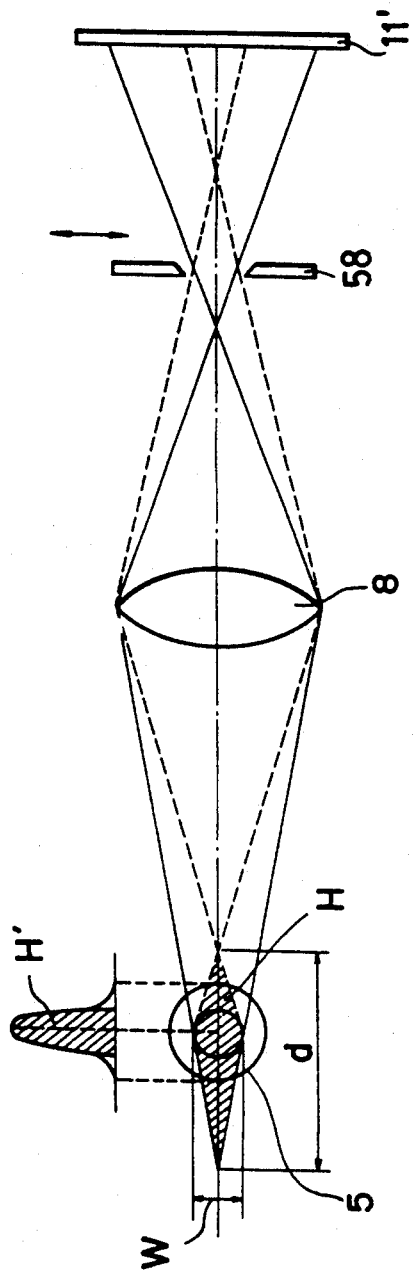
FIGS. 11a and 11b are for illustrating the effect of the ND filter on the alignment of the mask.

Problems involving the use of the ND filter holder 59 to reduce the amount of light will now be described with reference to FIGS. 11a and 11b. The mask alignment is performed by monitoring the intensity of light scattered by the medium in the measurement zone H. The light scattered by the medium, if it is limited by the mask 58, is too week to be detected when the P-polarized light is projected and the ND filter is used. FIG. 11a shows the focal depth conjugate to the mask 58, as produced by the imaging lens 8, when no ND filter is used between the mask 58 and the measuring plane 11a face 10a of the photosensor 11. FIG. 11a also shows the light intensity distribution H' obtained from the photosensor 11 in the measurement zone H in the depth d. As can be seen from FIGS. 11a and 11b, in the beam waist of the laser beam 5 there is formed a particle measurement zone H with the width w of a field of view that corresponds to the width of the aperture of the mask 58.

Referring to FIG. 11a, as shown by the light distribution H' that can be detected by the photosensor 11, there is a portion of very strong intensity in the center of the laser beam 5. Therefore, by moving the mask 58 up or down to find the maximum intensity of scattered light detected by the photosensor 11, the measurement zone H corresponding to the mask 58 can be brought to an optimum position in the center of the laser beam 5.

Figure 11B:
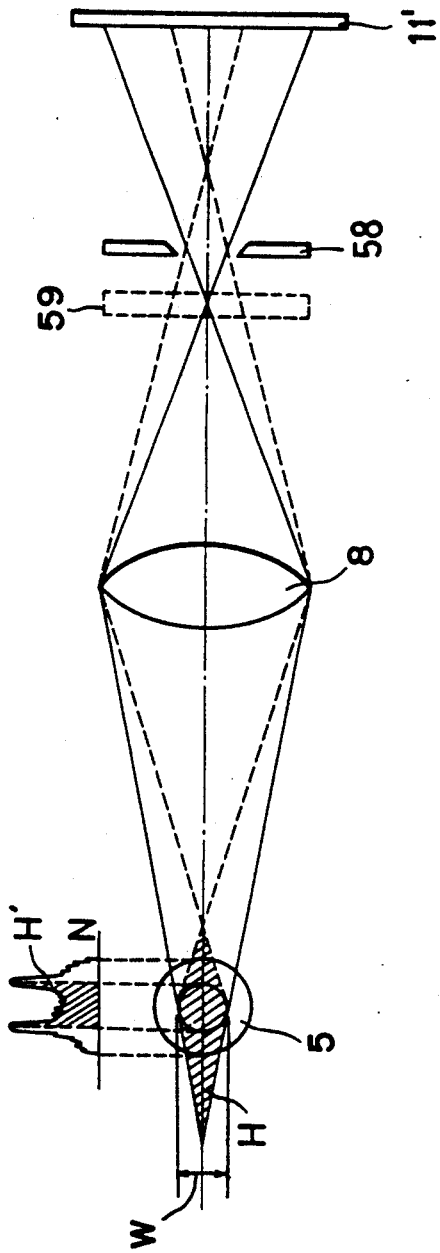

However, when a ND filter is used in the optical path, there is considerable variation in the light intensity distribution as obtained by the photosensor 11, as shown by H' in FIG. 11b. As mentioned above, the photon counting process is used to measure the intensity of the scattered light which results in fluctuation of the measured intensity. Because the extent of the light intensity fluctuation is proportional to the quotient of the standard deviation of the fluctuation $\sqrt{\mu}$ divided by the average value of the light intensity $\mu$, a reduction in the light intensity $\mu$ that can be obtained with the photosensor 11 when an ND filter is used to reduce the amount of light, causes a consequent increase in the amount of fluctuation, making it difficult to determine the optimum position for the mask 58 in accordance with variations in the output of the photosensor 11.

Figure 12:
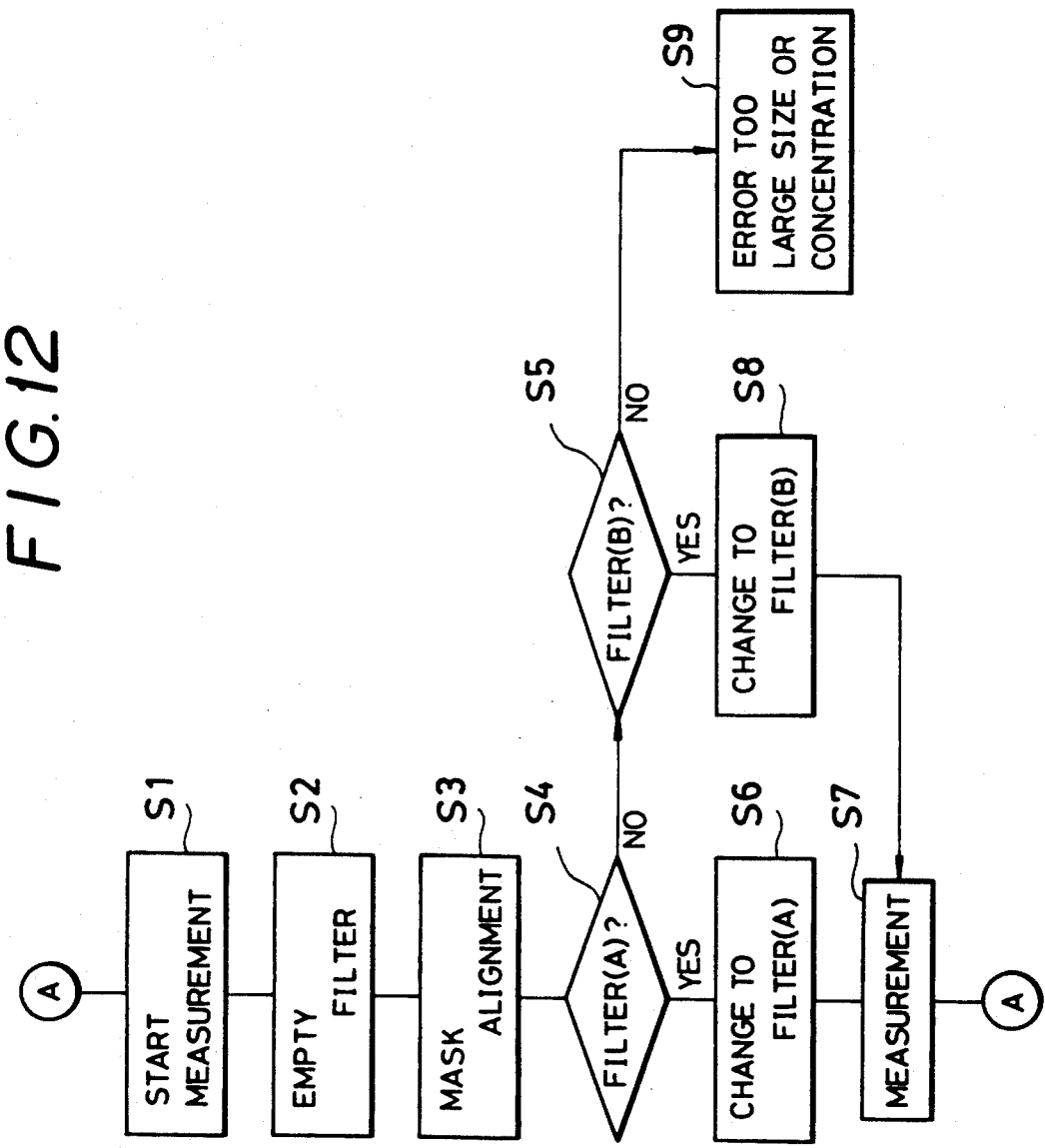
FIG. 12 is a flowchart of the measurement procedure according to the invention.

FIG. 12 is a flowchart of the measurement control process of the controller 100 in this embodiment to overcome the above drawback. The control program is stored in a ROM or like ( not shown ) connected to the controller 100.

When an instruction to start the measurement is issued, in step S1 ( FIG. 12 ) the controller 100 activates the laser light source 1 and light intensity in the measurement zone is measured by means of the photosensor 11. For the initial measurement state, in step S2 the ND filter holder 59 is rotated by the actuator 59a to bring the empty aperture C into the optical path of the light receiving system. In step S3 the mask 58 is aligned using a known procedure, by monitoring the output of the photosensor 11.

In step S4 and S5, the intensity of light scattered by particles in the medium is measured by means of the photosensor 11, and an appropriate ND filter is selected. In step S4 the output of the photosensor 11 is checked and it is judged whether or not use of ND filter A would bring the incident light intensity on the photosensor 11 within the dynamic range of the photosensor 11. If the judgment is positive, in step S6 the actuator 59a is operated to bring ND filer A into the optical path.

Similarly, in step S5 it is judged whether or not use of ND filter B would bring the incident light intensity within the dynamic range of the photosensor 11, and, if the judgment is positive, in step S8 the actuator 59a is operated to bring ND filter B into the optical path. If in step S5 it is judged that measurement in not possible even with ND filter B, the procedure is terminated in step S9 on the ground that the particles are too large.

Upon completion of steps S6 and S8, in step S7 the particles are measured in accordance with a known method (for example, U.S. Pat. No 4,830,494) of evaluating scattered light intensity. In step S7 the photon counting method is employed for this evaluation of scattered light intensity.

With the above arrangement, even when the intensity of the scattered light is strong and must be sharply reduced to bring it within the dynamic range of the photosensor 10 for measurement purpose, precise mask alignment is still possible.

In addition, with photon counting being used to evaluate the scattered light intensity, more precise measurement is possible because the system is less prone to the effects of electrical drift and noise compared with when scattered light intensity is processed as an analog quantity.

Furthermore, as the ND filter employed to reduce the light amount is a plan parallel plate, there is no risk of the measuring light beam moving off the photosensitive face of the photosensor 11 even if the filter is located between the mask 58 and the photosensor 10.

While in the foregoing the embodiment has been described in terms of the two ND filters A and B, it is also possible to use a plurality of filters in which the empty aperture will still enable the mask to be aligned with good precision.

In accordance with this arrangement, light can be reduced appropriately in accordance with the size of the particles to be measured, thereby providing accurate measurement over a wide range of particle sizes.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A particle measurement apparatus for measuring particle properties in which a laser beam is projected into a detection region in a medium containing particles to be measured, and a photoelectric detector having a predetermined dynamic range is used to detect the laser light scattered by the particles in the gaseous or liquid medium to produce signals which are evaluated to measure the particle properties, comprising:

a mask disposed in front of the photoelectric detector to limit the scattered light by the medium that impinges thereon;

mask alignment means for aligning the mask to an optimum position;

filter means having a plurality of filters each having a predetermined transmittance to regulate the intensity of the scattered light that impinges on the photoelectric detector; and means for selecting one of the filters without attenuation of light during mask alignment and one of the filters with a predetermined transmittance after mask alignment so that the intensity of the scattered light comes within the dynamic range of the photoelectric detector.

2. A particle measurement method for measuring particle properties in which a laser beam is projected into a detection region in a gaseous or liquid medium containing particles to be measured, and a photoelectric detector having a predetermined dynamic range is used to detect the laser light scattered by the particles in the medium to produce signals which are evaluated to measure the particle properties, comprising the steps of:

projecting the laser beam having either a first polarization or a second polarization into the medium containing particles;

detecting the light scattered by the particles;

determining the particle size using a photon counting method;

automatically regulating the polarization of the laser beam to be the first polarization when the particles are smaller than a predetermined size and regulating the polarization of the laser beam to be the second polarization when the particles are larger than the predetermined size;

automatically regulating the intensity of the scattered light to be within the dynamic range of the photoelectric detector when the laser light having the second polarization scattered by the particles is not within the dynamic range of the photoelectric detector; and measuring the properties of the particles by evaluating the signals produced by the photoelectric detector.

3. A particle measurement method as set forth in claim 2, wherein the first polarization is S-polarization and the second polarization is P-polarization.

4. A particle measurement method as set forth in claim 3, wherein the regulation of the intensity of the scattered light is achieved by using a filter selected from a set of filters each having a different transmittance, said filter being selected dependent upon the intensity of the scattered light to regulate the intensity of the scattered light to be within the dynamic range of the photoelectric detector.

5. A particle measurement method as set forth in claim 4, wherein a first filter from the set of filters is used to regulate the intensity of the scattered light and when the scattered light is still not within the dynamic range of the photoelectric detector, each successive filter from the step of filters is used having a lower respective transmittance until the scattered light is within the dynamic range of the photoelectric detector and measurement takes place, and a measurement error signal results when there is not filter that results in measurement.

6. A particle measurement apparatus for measuring particle properties in which a laser beam is projected into a detection region in a gaseous or liquid medium containing particles to be measured, and a photoelectric detector having a predetermined dynamic range is used to detect the laser light scattered by the particles in the medium to produce signals which are evaluated to measure the particle properties, comprising:

means for projecting the laser beam having either a first polarization or a second polarization into a medium containing particles;

means including a photoelectric detector having a predetermined dynamic range for detecting the light scattered by the particles and producing a light intensity signal;

means receptive of the light intensity signal for determining the particle size using a photon counting method;

means for regulating the polarization of the laser beam to be the first polarization when the particles are smaller than a predetermined size and regulating the polarization of the laser beam to be the second polarization when the particles are larger than the predetermined size;

means responsive to the light intensity signal for regulating the intensity of the scattered light to be within the dynamic range of the photoelectric detector when the laser light having the second polarization scattered by the particles is not within the dynamic range of the photoelectric detector; and means for measuring the properties of the particles by evaluating the light intensity signal produced by the photoelectric detector.

7. A particle measurement apparatus as set forth in claim 6, wherein the first polarization is S-polarization and the second polarization is P-polarization.

8. A particle measurement apparatus as set forth in claim 7, wherein the means for regulating the intensity of the scattered light comprises:

a set of filters each having a different transmittance; and means for selecting one of said filters in response to the light intensity signal.

9. A particle measurement apparatus as set forth in claim 7, wherein the means for regulating the intensity of the scattered light comprises:

a pair of polarizing filters positioned, configured and dimensioned to attenuate the scattered light that would be detected by the means for detecting the light scattered by the particles, one of said polarizing filters being at a fixed position and the other polarizing filter rotatably mounted; and a means for rotating the rotatably mounted polarizing filter to continuously increase or decrease the attenuation of the scattered light in response to the light intensity signal.

* * * * *